(12) United States Patent
Carlino et al.

(10) Patent No.: US 7,453,004 B2
(45) Date of Patent: Nov. 18, 2008

(54) PROCESS FOR PREPARING ALOE-EMODIN

(75) Inventors: Stefano Carlino, Collombey (CH); Guido Di Napoli, Collonge-Bellerive (CH)

(73) Assignee: Laboratoire Medidom S.A., Geneva (CH)

( * ) Notice: Subject to any disclaimer, the term of this patent is extended or adjusted under 35 U.S.C. 154(b) by 18 days.

(21) Appl. No.: 11/667,087

(22) PCT Filed: Nov. 11, 2005

(86) PCT No.: PCT/IB2005/003375

§ 371 (c)(1), (2), (4) Date: May 4, 2007

(87) PCT Pub. No.: WO2006/051400

PCT Pub. Date: May 18, 2006

(65) Prior Publication Data

US 2008/0125611 A1 May 29, 2008

(30) Foreign Application Priority Data

Nov. 12, 2004 (EP) .................................. 04405702

(51) Int. Cl.
*C07C 45/27* (2006.01)
*C07C 45/00* (2006.01)
*C09B 1/00* (2006.01)

(52) U.S. Cl. ........................ 552/208; 552/224; 568/321

(58) Field of Classification Search ................. 552/208, 552/224; 568/321
See application file for complete search history.

(56) References Cited

U.S. PATENT DOCUMENTS 5,652,265 A  7/1997  Vittori et al.

FOREIGN PATENT DOCUMENTS

EP  0 928 781 B1  3/2002

OTHER PUBLICATIONS

Oesterle, O. A. et al., "Aloin", CAPLUS, vol. 47, 1910, pp. 717-721, XP002341227.
Seel, E., et al., "Products of oxidation of aloin", CAPLUS, vol. 112, No. 1. 1917, XP002341228.
Vogt, E. et al. "Anthraquinones and anthraquinone glycosides. XX. Partial synthesis of chrysophanol and chrysazin anthraquinones and glucosides. 1", CAPLUS, vol. 46, No. 7, 1971, pp. 431-440, XP002341229.

*Primary Examiner*—Sikarl A Witherspoon
(74) *Attorney, Agent, or Firm*—Baker & Daniels LLP

(57) ABSTRACT

A process for preparing aloe-emodin from aloin by oxidizing aloin by treatment with an oxygen-containing gas in the presence of an acid. The aloe-emodin may be used for the production of rhein and diacerein by oxidizing aloe-emodin by treatment with a chromium-free oxidizing medium to obtain rhein and purifying the rhein obtained. The rhein may be acetylated to obtain diacerein.

18 Claims, No Drawings

PROCESS FOR PREPARING ALOE-EMODIN

BACKGROUND OF THE INVENTION

The present invention relates to a process for preparing aloe-emodin from aloin. Further there is provided a process for preparing rhein and diacerein from aloin.

Diacerein is known as being useful in the treatment of diseases associated with an abnormal degeneration of the connective tissue, and more particularly in the treatment of inflammatory states of the joints and of the connective tissue such as rheumatoid arthritis, osteoarthritis, and osteoporosis, of acute respiratory syndrome in adults, or of pulmonary emphysema.

The most known process for preparing diacerein from aloin comprises acetylation of aloin and subsequent chromic oxidation of the acetylated product to obtain diacerein.

For example, WO-A-98 56750 (Synteco) discloses a process for preparing diacerein from aloin which comprises acetylating aloin to obtain acetylbarbaloin, oxidizing acetylbarbaloin with an oxidizing agent consisting of chromic anhydride in acetic acid solution to obtain crude diacerein and subsequently purifying crude diacerein.

In such a process, the chromic oxidation occurs only if aloin used as the starting material has a high degree of purity.

Further, use of hexavalent chromium compounds such as chromic anhydride ($CrO_3$) is subjected to stringent regulations in view of their very high toxicity and carcinogenicity, as well as on their harmful effect on the environment and at the present time, and in the future authorities may limit the use of hexavalent chromium compounds in the industry.

Still further, to reach a purity of pharmaceutical grade, crude diacerein obtained by chromic oxidation of acetylbarbaloin must be subjected to a subsequent purification process for obtaining a diacerein substantially free from impurities, and more particularly free from aloe-emodin and free from any traces of chromium.

However, purification of crude diacerein to obtain diacerein free from aloe-emodin and free from chromium residues is known to be particularly critical.

Therefore, many processes have been proposed in the literature for purifying crude diacerein obtained by chromic oxidation of acetylbarbaloin (see for example EP-A-0 636 602 (Laboratoire Medidom), WO-A-00/68179 (Synteco), WO-A-98/56750 (Synteco), WO-A-01/96276 (Synteco), WO-A-2004/050601 (Synteco)).

However, known processes for purifying crude diacerein obtained by chromic oxidation of acetylbarbaloin suffer from several drawbacks in that they are complex multi-step processes and/or use toxic solvents or reagents, and/or provoke a remarkable decrease in the yield of pure diacerein with respect to crude diacerein.

As an alternative to preparing diacerein from aloin via the acetylation of aloin to obtain acetylbarbaloin, there have been proposed in the literature processes for the preparation of diacerein starting from aloe-emodin. For example there has been described the preparation of diacerein via oxidation with hexavalent chromium of aloe-emodin ("Sostanze farmaceutiche", Italian translation and review by R. Longo, OEMF, Milan, 1988, p. 596, of "Pharmazeutische Wirkstoffe, Synthesen, Patente, Anwedungen", George Thieme Verlag, Stuttgart-New York, 1982-1987).

In the literature there have been described processes for the preparation of aloe-emodin by semi-synthetic preparative processes. Chen When-Ho et al. (Journal of Nanjing College of Pharmacy, 1986, 17(1), 1-4; Chemical Abstract, Vol. 105, 1986, 105:226138z), and U.S. Pat. No. 5,652,265 of Vittori et al., describe the preparation of aloe-emodin by treatment of aloin with $FeCl_3$.

However known processes for the preparation of aloe-emodin suffer from several drawbacks, in that the known synthetic processes require the use of metallic reagents, or other harmful or toxic substances, and require complicated purification processes to remove residues of the metallic or otherwise harmful reagents.

SUMMARY OF THE INVENTION

Therefore, there is a need for a process for preparing aloe-emodin from aloin which does not require the use of toxic or harmful substances, which does not require complex purification processes and which provides aloe-emodin with a good yield and level of purity.

There is also a need for a process for preparing diacerein from aloin which does not comprise chromic oxidation and which does not require complex purification process.

After extensive studies, the present inventors have found that aloe-emodin may be easily and advantageously prepared from crude aloin without the need for chromium compounds or other toxic or harmful substances, using a process which can be easily scaled up to industrial level.

The present invention has been achieved on the basis of these results.

Disclosed herein is a process for preparing aloe-emodin from aloin comprising treating aloin with an oxygen-containing gas in the presence of an acid. The acid used in oxidizing aloin is preferably nitric acid or sulphuric acid.

The aloin is advantageously dissolved in a polyhydric alcohol, preferably ethylene glycol or propylene glycol, before treatment with the oxygen-containing gas.

Preferably, the aloin is dissolved in the polyhydric alcohol at a concentration up to 70% w/v.

In a preferred embodiment of the present invention, the aloin used is crude aloin extracted from Aloe-Vera comprising at least 1% pure aloin, and preferably from 30 to 50% pure aloin.

Preferably, oxidation of the aloin is carried out at a temperature ranging from 100 to 120° C., under an oxygen-saturated atmosphere.

In a preferred embodiment of the present invention, the oxygen-containing gas is preferably selected from a group including oxygen gas and air.

The aloe-emodin may be advantageously prepared from crude aloin, e.g. as extracted from Aloe-Vera.

Advantageously, aloe-emodin may be obtained from aloin by the present process without the need for metallic reagents, avoiding the need for complex purification processes to remove residual metal ions.

Further disclosed is a process for preparing rhein or diacerein from the thus-obtained aloe-emodin, comprising the steps of oxidizing the aloe-emodin by treatment with a chromium-free oxidizing medium to obtain rhein, and purifying the rhein.

The chromium-free oxidizing medium may include a salt of nitrous acid, advantageously sodium nitrite. The chromium-free oxidizing medium may advantageously further include boric acid dissolved in sulphuric acid, whereby the oxidation is preferably carried out at a temperature ranging from 110 to 130° C.

The purification of rhein may advantageously be performed by liquid-liquid partition between an apolar aprotic organic solvent which is not miscible in water and an aqueous phase having a pH in the range from 9 to 9.5.

Preferably, in the step of purification of rhein, the apolar aprotic organic solvent which is not miscible in water is selected from toluene and dichloromethane. In a preferred embodiment of the present invention, purification by liquid-liquid partition is carried out by means of a continuous liquid-liquid extraction.

The rhein obtained may be acetylated by treatment with an acetylating agent, preferably acetic anhydride, to obtain diacerein.

Advantageously rhein and diacerein may thus be obtained from aloin, via oxidation to aloe-emodin, without carrying out chromium oxidation.

Other objects and advantageous features of the present invention will be apparent from the claims and the following detailed description and examples.

DETAILED DESCRIPTION OF THE INVENTION

The process of the present invention comprises oxidizing aloin represented by the following formula (I):

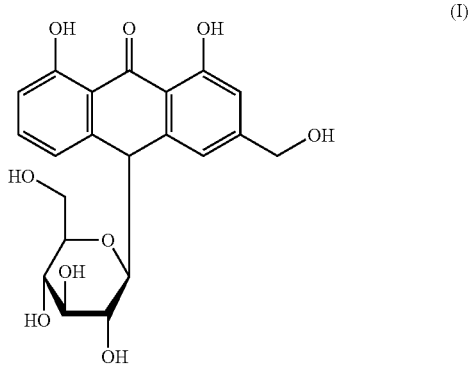

to obtain aloe-emodin represented by the following formula (II):

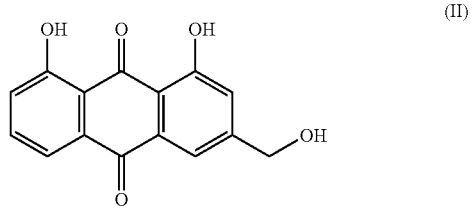

The aloin is oxidized by treatment with an oxygen-containing gas in a reaction medium in the presence of an acid.

According to the present invention, the degree of purity of aloin as the starting material is not critical.

Therefore, it must be understood that in the present application, the term "aloin" is intended to mean aloin having any degree of purity, unless otherwise is indicated.

As an example, aloin as the starting material may be pure aloin, commercial aloin or crude aloin, preferably crude aloin in the form of an extract from different plant species containing at least 1% pure aloin, and more preferably crude aloin extracted from Aloe species containing at least 30% pure aloin, for example from 30 to 50% pure aloin.

Using crude aloin extracted from Aloe containing from 30 to 50% pure aloin is particularly advantageous from the point of view of production costs.

For the oxidation reaction any suitable reaction medium may be used. A suitable reaction medium includes any solvent in which aloin is soluble to form a stable solution and which is capable of supporting the temperature required for the oxidation reaction. Advantageously the reaction medium is an organic solvent.

According to a preferred embodiment of the invention the reaction medium is a polyhydric alcohol. The polyhydric alcohol used as the reaction medium may be any polyhydric alcohol which dissolves aloin. Preferably, polyhydric alcohols used for dissolving aloin are dihydric alcohols such as ethylene glycol, propylene glycol, 1,4-butane-diol, 1,5-pentane-diol and trihydric alcohols such as glycerol, manitol, sorbitol, without being limited to these.

Polyhydric alcohols are particularly suitable as a reaction medium as aloin dissolves readily in polyhydric alcohols, oxygen is readily soluble in polyhydric alcohols at the temperature at which the oxidation reaction is carried out, and aloe-emodin is poorly soluble in polyhydric alcohols. Further, the polyhydric alcohols are capable of supporting the temperatures at which the oxidation reaction is carried out, and are inert to the oxidation reaction.

In a preferred embodiment of the present invention, polyhydric alcohol used for dissolving aloin is selected from ethylene glycol, propylene glycol and glycerol. Ethylene glycol is preferred due to its low toxicity, relatively high flash point of 111° C., and low industrial cost.

Preferably, crude aloin is dissolved in the polyhydric alcohol at a concentration up 70% w/v.

In order to proceed with the oxidation of aloin in the presence of an acid, an acid is added slowly to the aloin-containing solution, preferably under an inert atmosphere, for example nitrogen or argon atmosphere, before carrying out the oxidation.

In a preferred embodiment of the present invention, the aloin-containing solution may be heated at a temperature in the range from 80-160° C., more preferably at a temperature in the range from 100-120° C.

Preferably, the acid is a strong mineral acid, and may be for example nitric acid, sulphuric acid, trichloroacetic acid or perchloric acid. In a preferred embodiment, the acid is selected from nitric acid and sulphuric acid. The acid is preferably added in an amount ranging from 0.1 to 5 molar equivalents with respect to pure aloin content.

Oxidation of aloin dissolved in the polyhydric alcohol with an oxygen-containing gas in the presence of an acid may be carried out for example by introducing the oxygen-containing gas in a continuous way into the heated solution or by putting the heated solution under an oxygen-containing gas over-pressure. Preferably the oxidation reaction is carried out under an oxygen-containing gas over-pressure. The oxygen-containing gas is preferably oxygen gas or air.

Where oxidation of aloin is carried out by subjecting the heated aloin solution to a gas over-pressure of oxygen, the gas pressure in the reaction chamber may suitably be 0.1-6 bar absolute pressure, preferably 1.2-2 bar, for example 1.5 bar. If the oxidation is carried out by subjecting the heated aloin solution to a gas over-pressure of air, the reaction is preferably carried out under a gas pressure of 1.2-10 bar absolute pressure, preferably 2-2.5 bar.

The reaction time will depend on the reaction conditions. Oxidation of aloin under an oxygen-containing gas over-pressure may generally be carried out over 3-12 hours preferably 4-6 hours.

If oxidation of aloin is carried out by introducing air in a continuous way into the heated solution, air is preferably introduced into the heated solution at a flow rate of 5-50 L/min.

If oxidation of aloin is carried out by introducing oxygen gas in a continuous way into the heated solution, oxygen gas is preferably introduced into the heated solution at a flow rate of 1-10 L/min.

The reaction time of the oxidation will depend on the reaction conditions. Determination of the reaction time and the degree of conversion of aloin to aloe-emodin may be obtained by conventional techniques of analysis, for example HPLC.

As an example, a study of the influence of the amount of oxygen gas continuously introduced into a heated aloin-containing solution has been carried out.

The heated aloin-containing solution used in this study has been prepared by dissolving 72 g crude aloin containing 39% pure aloin in 250 ml ethylene glycol, pouring the solution into a one-liter reactor, warming it to 120° C. in a nitrogen atmosphere and adding over 20 minutes 7.58 g $HNO_3$ diluted in 50 ml ethylene glycol.

Oxygen gas at various flow rates was introduced into said heated aloin-containing solution and samples were withdrawn every hour from the reaction mixture and analyzed by HPLC.

The results are summarized in Table 1 below.

TABLE 1

| time [h] | $O_2$ 8[L/min] | $O_2$ 4[L/min] | $O_2$ 2[L/min] | $O_2$ 1[L/min] |
|---|---|---|---|---|
| 0 | 1.0% | 1.0% | 0.9% | 0.9% |
| 0.5 | 15.7% | 23.8% | 23.4% | 12.0% |
| 1 | 29.0% | 36.5% | 36.6% | 17.1% |
| 2 | 37.1% | 49.1% | 50.8% | 21.4% |
| 3 | 44.8% | 56.6% | 55.8% | 22.8% |
| 4 | 40.6% | 58.7% | 57.0% | 20.8% |
| 5 | 45.5% | 60.2% | 59.5% | 22.5% |
| 6 | 45.6% | 61.0% | 58.3% | 21.8% |

From Table 1, it can be seen that in the above specific conditions, the maximum yield of oxidation of aloin into aloe-emodin occurs after 5-6 hours if oxygen is introduced at a flow rate ranging from 2 to 4 [L/min].

The oxidation reaction will be usually followed by a conventional treatment of the reaction mixture to isolate aloe-emodin. This may comprise for example pouring the reaction mixture into water, extracting aloe-emodin using an organic solvent, for example toluene or dichloromethane, precipitating aloe-emodin in an alcohol, for example ethanol, filtering aloe-emodin and drying aloe-emodin.

The isolation of aloe-emodin from the reaction mixture may advantageously comprise extraction and purification by liquid-liquid partition, which may be followed by crystallization of the aloe-emodin in pure form.

For the extraction and purification the oxidized reaction mixture may preferably first be filtered and washed. The washing may advantageously comprise washing with excess reaction medium, e.g. polyhydric alcohol, to remove residual compounds soluble therein, and washing with water to remove any residual reaction medium, e.g. polyhydric alcohol. Additionally the filtrate may be washed with aqueous solution with pH adjusted to pH 9-11 to remove residual compounds soluble in water at basic pH.

Aloe-emodin may then be extracted by solvent extraction using any suitable organic solvent in which aloe-emodin is soluble, for example methylene chloride or toluene. The solvent solution containing aloe-emodin is subjected to a liquid-liquid partitioning with an aqueous buffered solution, pH adjusted to pH 9 to 11, preferably pH 10. A pH above 11 is not suitable as at such a pH aloe-emodin is soluble in aqueous solution and would be lost. Any buffer having a pK in the range of 9-11 may be used, for instance glycine buffer, KCl-boric acid-NaOH buffer, carbonate buffer, CHES (2-(N-Cyclohexylamino)ethanesulfonic acid) buffer, CAPSO (3-(Cyclohexylamino)-2-hydroxy-1-propanesulfonic acid) buffer, AMP (2-Amino-2-Methyl-1-propanol) buffer, CAPS (3-(Cyclohexylamino)-1-propanesulfonic acid) buffer. The aloe-emodin containing solvent solution is then subjected to a second liquid-liquid partitioning step with an alkaline aqueous solution. The pH of the aqueous solution is adjusted to above pH 11 with an organic base. The organic base may be an alkaline metal hydroxide, such as sodium hydroxide.

The liquid-liquid extraction may for example be a batch liquid-liquid extraction or a continuous liquid-liquid extraction. If said liquid-liquid extraction is a batch liquid-liquid extraction, it is preferably repeated until aloe-emodin having the required degree of purity is obtained. If the liquid-liquid extraction is a continuous liquid-liquid extraction, it is preferably continued until aloe-emodin having the required degree of purity is obtained. In a preferred embodiment of the present invention, the liquid-liquid extraction is a continuous liquid-liquid extraction.

Advantageously, the extraction solvent can be recovered and recycled for further use in the extraction process.

The liquid-liquid extraction may be followed by a conventional treatment of the aqueous phase to isolate pure aloe-emodin. This may comprise, for example, acidifying the basic aqueous phase containing aloe-emodin with an inorganic acid, such as hydrochloric acid, to precipitate aloe-emodin, filtration, washing with purified water, and drying the aloe-emodin.

Aloe-emodin obtained according to the process of the present invention has a purity degree of 95% or more, generally about 98.0-99.5%.

According to the one embodiment of the present invention, aloe-emodin produced by the above-described oxidation of aloin, may be oxidized to obtain rhein represented by the following formula (III):

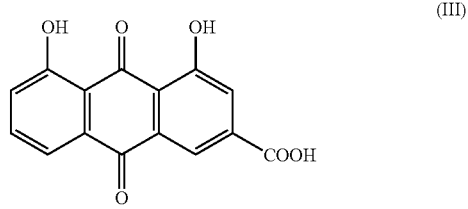

Aloe-emodin is advantageously oxidized in a chromium-free oxidizing medium. The step of oxidation of aloe-emodin to rhein in a chromium-free oxidizing medium may be carried out by known methods, for instance as described in EP 0 928 781 A1, Laboratoire Medidom S.A. The chromium-free oxidizing medium may comprise a salt of nitrous acid, in particular an inorganic salt, such as salts of alkaline or alkaline-earth metals, for instance sodium nitrite, potassium nitrite, or calcium nitrite. Preferably, sodium nitrite is used.

The reaction medium preferably comprises an acid, for example a mineral acid, in particular a strong mineral acid, such as sulphuric acid or boric acid, or alternatively a carboxylic acid, possibly halogenated, such as acetic acid, trichloro-acetic acid, or a sulphonic acid, such as methanesulphonic acid. The chromium-free oxidizing medium comprises preferably sodium nitrite dissolved in sulphuric acid, optionally with the addition of boric acid.

The oxidation may be carried out for example by adding slowly aloe-emodin to the chromium-free oxidizing medium comprising, for instance, sodium nitrite dissolved in sulphuric acid, or sodium nitrite dissolved in sulphuric acid and boric acid, to obtain crude rhein.

In a preferred embodiment, the chromium-free oxidizing medium comprising sodium nitrite dissolved in sulphuric acid, and optionally boric acid, is heated at a temperature in the range from 80-160° C., and more preferably in the range from 110-130° C., before the addition of aloe-emodin.

The reaction time will depend on the reaction conditions and will usually lie in the range from 2 to 4 hours.

The oxidation reaction may be followed by a conventional treatment of the reaction mixture to isolate crude rhein. This may comprise for example pouring the reaction mixture into distilled water at 2° C. to precipitate rhein, filtering rhein, washing rhein with distilled water at 2° C. and drying rhein.

The purity of rhein obtained by the chromium-free oxidation of aloe-emodin is dependent on the purity of the starting aloe-emodin. Rhein obtained by the above chromium-free oxidation process according to the invention, from aloe-emodin prepared by the oxidation of aloin according to the process of the present invention has a purity degree of around 90% -95%.

In order to remove all aloe-emodin residues and other contaminants, rhein obtained by the above oxidation process is subjected to a purification step.

This purification step advantageously comprises purifying rhein by liquid-liquid partition between an aprotic apolar organic solvent which is not miscible in water and an aqueous phase having a pH in the range from 7,5 to 11. In a preferred embodiment of the present invention, the pH is in the range from 9 to 9,5.

In the purification step, the rhein obtained by oxidation of aloe-emodin will preferably first be put into water to obtain an aqueous solution containing rhein. Preferably, the aqueous solution contains 10 mg rhein per 1 ml water.

After dissolution of rhein into water, the pH of the aqueous solution containing rhein is adjusted to a pH value ranging from 9 to 9.5 with an inorganic base. The inorganic base may be for example an alkaline metal hydroxide such as sodium hydroxide or potassium hydroxide. In a particularly preferred embodiment of the present invention, said inorganic base is sodium hydroxide, and more preferably sodium hydroxide 5 M.

The aqueous solution containing rhein and having a pH in the range from 9 to 9.5 is subjected to a liquid-liquid extraction with an aprotic apolar organic solvent which is not miscible in water. The aprotic apolar organic solvent which is not miscible in water may be for example toluene, dichloromethane, hexane, heptane, pentane, ether, tetrahydrofurane (THF). In a particularly preferred embodiment, said aprotic apolar organic solvent which is not miscible in water is toluene or dichloromethane.

The liquid-liquid extraction may for example be a batch liquid-liquid extraction or a continuous liquid-liquid extraction. If said liquid-liquid extraction is a batch liquid-liquid extraction, it is preferably repeated until rhein having the required degree of purity is obtained. If the liquid-liquid extraction is a continuous liquid-liquid extraction, it is preferably continued until rhein having the required degree of purity is obtained. The required degree of purity of rhein will depend on the subsequent use of rhein.

In a preferred embodiment of the present invention, the liquid-liquid extraction is a continuous liquid-liquid extraction which is continued until the rhein contains less than 2 ppm of aloe-emodin (HPLC).

The liquid-liquid extraction will be usually followed by a conventional treatment of the aqueous phase to isolate pure rhein. This may comprise for example acidifying the aqueous phase containing pure rhein until pH 1 with an inorganic acid, for example hydrochloric acid, to precipitate rhein, filtering rhein, washing rhein with distilled water at 2° C. and drying rhein.

If needed, the thus produced rhein may be further acetylated according to an optional acetylation step to obtain diacerein as represented by the following formula (IV):

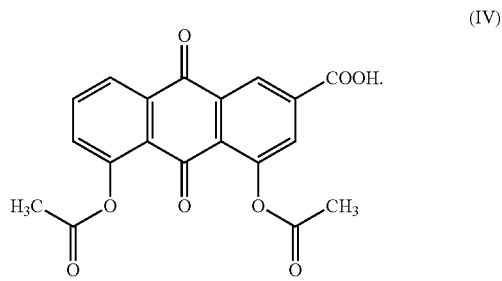

(IV)

The acetylation of rhein may be carried out by treatment of rhein with an acetylating reagent which can be chosen from those known to the person skilled in the art. However, in a preferred embodiment, the acetylating agent is acetic anhydride.

The acetylation may be carried out in various organic solvents provided that they are inert, or in any case compatible with the reaction conditions such a glacial acetic acid. However, in a preferred embodiment, acetic anhydride is used as the reaction solvent.

Acetylation of rhein with acetic anhydride is preferably carried out in the presence of an acid as a catalyst. In a preferred embodiment, said acid used as a catalyst is sulphuric acid.

Acetylation of rhein with acetic anhydride is preferably carried out at a temperature ranging from 20 to 50 ° C., more preferably, from 30 to 40° C., for 3 to 6 hours, yet more preferably for 4 to 5 hours.

The acetylation reaction will be usually followed by a conventional treatment of the reaction mixture to isolate diacerein. This may comprise for example pouring the reaction mixture in distilled water at 4° C., filtering diacerein, washing diacerein with distilled water and drying diacerein. If needed, diacerein may be further purified by recrystallization in a solvent such as ethanol, acetone or isopropanol or any other appropriate solvent.

According to the process of the present invention, aloe-emodin may be prepared from aloin without the need for metallic reagents, or other toxic or harmful substances, and without the need for complex purification processes to remove residual metal ions. According to the process described herein aloe-emodin may be obtained from aloin at a good yield and level of purity.

The process according to the invention is also economical since crude aloin may be used as the starting material, and inexpensive reagents and solvents may be used in the process. Moreover, the process is easy to carry out even in an industrial scale.

According to the one embodiment of the present invention, rhein and diacerein may advantageously be obtained from aloin without carrying out chromium oxidation, and without using toxic or harmful reagents or solvents.

EXAMPLES

The starting materials, reagents and solvents used in the following synthesis are all available products as specified below:

Crude Aloin: provided by Aloven (Braquismeto, Venezuela), assay 30-50%

Ethylene glycol: provided by Schweizerhall AG (Basel), assay 99.90 WT %

Dichloromethane: provided by Schweizerhall AG (Basel), assay 98-100%

Ethanol: provided by Schweizerhall AG (Basel), assay 98%

Toluene: provided by Schweizerhall AG (Basel), assay 100%

Nitric acid 65% : provided by Fluka AG (Buchs)

Boric acid: provided by Fluka AG (Buchs), assay 99.5%

Sodium nitrite: provided by Merck (Darmstadt Germany), assay 99.0%

Sulphuric acid: provided by Merck (Darmstadt Germany), assay 95-97%

Sodium hydroxide: provided by Fluka AG (Buchs), assay 98%

Acetic anhydride: provided by Fluka AG (Buchs), assay 99.5%

Preparation of Aloe-Emodin from Aloin

Example 1

Crude Aloin (72 g containing 39% pure aloin) was dissolved in ethylene glycol (250 ml). The solution was poured in a one-liter reactor and warmed at 120° C. under nitrogen atmosphere. When the temperature of 120° C. was reached, $HNO_3$ (7.58 g) diluted in ethylene glycol (50 ml) was added during 20 minutes. At this time, oxygen gas was introduced at a flow rate of 4 L/min by means of a sparger into the reactor. Samples were withdrawn every hour from reactor and analyzed by HPLC to determine the completion of the reaction. After 6 hours, the reaction was completed. Under these conditions, the conversion rate from aloin to aloe-emodin was 61%.

Isolation of aloe-emodin was then carried out by successively pouring the reaction mixture into water, extracting aloe-emodin with toluene or dichloromethane, evaporating toluene or dichloromethane, drying aloe-emodin (purity: 50%), precipitating aloe-emodin in ethanol, filtering aloe-emodin and drying aloe-emodin to obtain aloe-emodin 95-98% pure. The yield was in a range of 75% -95%.

Example 2

Under nitrogen atmosphere, crude Aloin (3.24 Kg, containing 36% pure aloin) was dissolved in ethylene glycol (13.5 l). Under continuous agitation 170 g of nitric acid (dissolved in ethylene glycol) were added over 5 minutes. The solution warmed to a temperature of 105° C. At this time nitrogen was washed out by the introduction of oxygen flow for 10 minutes. The reactor was then pressurized by the introduction of oxygen up to a pressure of 1.5 bars absolute pressure. The oxygen pressure was maintained at 1.5 bars absolute pressure for 5 hours. The reactor was then depressurized to ambient pressure and cooled to room temperature. Under these conditions, the conversion rate from aloin to aloe-emodin was 80%.

Isolation of aloe-emodin was then carried out. The reaction mixture containing aloe-emodin in suspension was passed through a stainless steel filter press under pressure (8 bars absolute for 1 hour). The filter cake was then washed with half volume (7 l) of ethylene glycol under pressure (8 bars absolute for 7-8 hours), followed by purified water (8 bars absolute pressure for 2 hours), glycine buffer (0.1 M at pH 10) for 20 min at 8 bars absolute pressure, and purified water (10 minutes at 8 bars absolute pressure). The filter cake was then partially dried by blowing with nitrogen at 11 bars absolute pressure.

Methylene chloride was then passed through the filter cake in a continuous manner to extract aloe-emodin. The methylene chloride solution was added to an aqueous solution buffered with glycine 0.1 M at pH 10, and the liquids separated using a liquid-liquid centrifuge. Buffer solution was continuously recirculated until saturation, after which new buffer was constantly added and saturated buffer constantly washed out to maintain a steady concentration in the reaction vessel. The methylene chloride solution, still containing aloe-emodin, was then added to an aqueous solution containing NaOH 1 M and the liquids separated using a liquid-liquid centrifuge. NaOH solution containing aloe-emodin was continuously recirculated until saturation, after saturation new NaOH 1 M solution was constantly added and NaOH solution saturated with aloe-emodin constantly washed out and collected elsewhere to maintain a steady concentration in the reaction vessel.

The solution of aloe-emodin in NaOH was then precipitated by the addition of hydrochloric acid. Fine orange needles of aloe-emodin were precipitated on lowering the pH to below 1. The precipitate was then filtered, washed with purified water and dried with hot nitrogen. The aloe-emodin obtained had a purity of 99%.

Oxidation of Aloe-Emodin to Rhein

Example 3

Oxidizing medium was prepared by dissolving sodium nitrite (255 g) in sulphuric acid (1.2 l). The oxidizing medium was heated to 120° C. and then aloe-emodin (100 g) was added slowly thereto. After completion of the oxidation reaction (3 hours), the reaction mixture was poured into distilled water (7.2 l) at 2° C. to precipitate rhein, and rhein is filtered and dried. Rhein having a degree of purity of 90-95% was obtained in a yield of more than 85%.

Purification of Rhein

Example 4

Crude rhein obtained in example 3 was put in water to obtain a solution having a concentration of rhein at 10 mg/ml. The pH was adjusted at 9-9.5 with sodium hydroxide sodium 5 M. The basic aqueous phase obtained was continuously extracted with dichloromethane until a satisfactory degree of purity is obtained (<2 ppm aloe-emodin, HPLC). Then, hydrochloric acid was added to the aqueous phase to adjust the pH to 1 in order to precipitate rhein. Precipitated rhein was filtered, washed with distilled water at 2° C. and dried. Rhein 99.5% pure with a yield of 90 to 95% was obtained.

Preparation of Diacerein

Example 5

Purified rhein (90 g) obtained in example 4 was dissolved in acetic anhydride (6.48 l) and the solution was cooled at 0° C. Then sulphuric acid (64.8 ml) was added thereto and the reaction mixture was warmed at 30° C. After completion of the reaction (4-5 hours), the reaction mixture was poured into distilled water at 4° C. and the precipitated diacerein was filtered, washed with distilled water and dried. Diacerein was obtained in a yield of more than 90%. The diacerein was recrystallized in ethanol. The diacerein obtained was more than 98% pure.

The invention claimed is:

1. A process for preparing aloe-emodin from aloin comprising oxidizing aloin by treatment with an oxygen-containing gas in a reaction stable medium in the presence of an acid.

2. A process according to claim 1 wherein the aloin is dissolved in a polyhydric alcohol.

3. The process according to claim 2, wherein the polyhydric alcohol is selected from ethylene glycol and propylene glycol.

4. The process according to claim 2 or 3, wherein the aloin is dissolved in the polyhydric alcohol at a concentration up to 70% w/v.

5. The process according to any one of claims 1 to 4, wherein the aloin is crude aloin extracted from plants having a purity of more than 1%.

6. The process according to any one of claims 1 to 5, wherein oxidation is performed at a temperature ranging from 100 to 120° C. in an oxygenated atmosphere.

7. The process according to any one of claims 1 to 6, wherein the acid is selected from nitric acid and sulphuric acid.

8. The process according to any one of claims 1 to 7, wherein the oxygen-containing gas is selected from oxygen gas or air.

9. The process according to any one of claims 1 to 8 further comprising purifying and isolating the aloe-emodin.

10. A process for preparing rhein or diacerein from aloin which includes the steps of:
   a) oxidizing aloin by treatment with an oxygen-containing gas in the presence of an acid to obtain aloe-emodin;
   b) oxidizing aloe-emodin by treatment with a chromium-free oxidizing medium to obtain rhein;
   c) purifying rhein obtained in step b);
   d) optionally acetylating rhein obtained in step c) using an acetylating agent to obtain diacerein.

11. The process according to claim 10, wherein in step c) purification of rhein includes performing a liquid-liquid partition between a apolar aprotic organic solvent which is not miscible in water and an aqueous phase.

12. The process of claim 11 wherein the aqueous phase has a pH in the range from 7.5 to 11.

13. The process according to any one of claims 10 to 12, wherein in step b), the chromium-free oxidizing medium includes sodium nitrite.

14. The process according to claim 13 wherein the oxidizing medium further comprises boric acid dissolved in sulphuric acid.

15. The process according to claim 13 or 14, wherein in step b), oxidation is performed at a temperature ranging from 110 to 130° C.

16. The process according to claim 11, wherein the apolar aprotic organic solvent which is not miscible in water is selected from toluene and dichloromethane.

17. The process according to claim 11 or 16, wherein said purification by liquid-liquid partition includes performing a continuous liquid-liquid extraction.

18. The process according to any one of claims 10 to 17, wherein in step d), the acetylating agent is acetic anhydride.

* * * * *